United States Patent [19]

Rhodes, Jr.

[11] 4,036,236
[45] July 19, 1977

[54] SURGICAL SAW

[75] Inventor: Earl H. Rhodes, Jr., Kalamazoo, Mich.

[73] Assignee: Stryker Corporation, Kalamazoo, Mich.

[21] Appl. No.: 619,580

[22] Filed: Oct. 6, 1975

[51] Int. Cl.² .................. A61B 17/14; B27B 33/02
[52] U.S. Cl. ................................. 128/317; 30/348; 30/355
[58] Field of Search ............... 30/348, 355, 392, 393, 30/394; 128/317

[56] References Cited

U.S. PATENT DOCUMENTS

| | | | |
|---|---|---|---|
| 486,426 | 11/1892 | Brooks | 30/348 |
| 1,727,648 | 9/1929 | Jarvis | 30/348 X |
| 1,929,838 | 10/1933 | Crane | 30/348 X |
| 2,503,961 | 4/1950 | Meunier | 30/355 UX |
| 2,550,347 | 4/1951 | Gruber | 30/348 X |
| 3,642,002 | 2/1972 | Otterstrom | 128/317 |
| 3,905,374 | 9/1975 | Winter | 128/317 |

Primary Examiner—Channing L. Pace
Attorney, Agent, or Firm—Blanchard, Flynn, Thiel, Boutell & Tanis

[57] ABSTRACT

A blade for a surgical saw having a handpiece, a chuck and drive means for reciprocating the chuck in an axial direction. The blade is long, relatively thin and has an integral ridge on one side thereof extending lengthwise thereof. The ridge is intermediate of and spaced from the lengthwise edges of the blade. The ridge is on one side only of the blade. A shank is secured to one end of the blade for engagement by the chuck.

2 Claims, 4 Drawing Figures

U.S. Patent  July 19, 1977  4,036,236
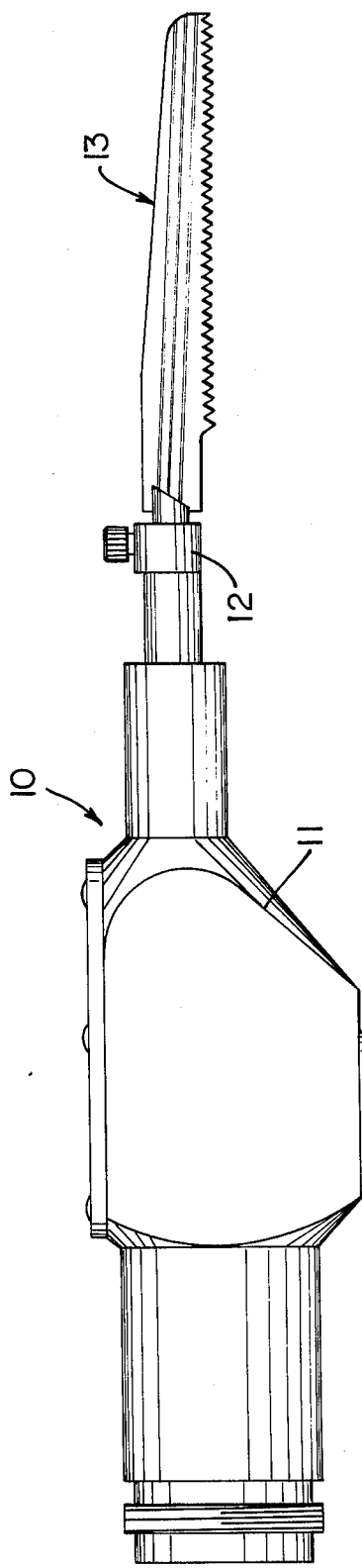
FIG.1
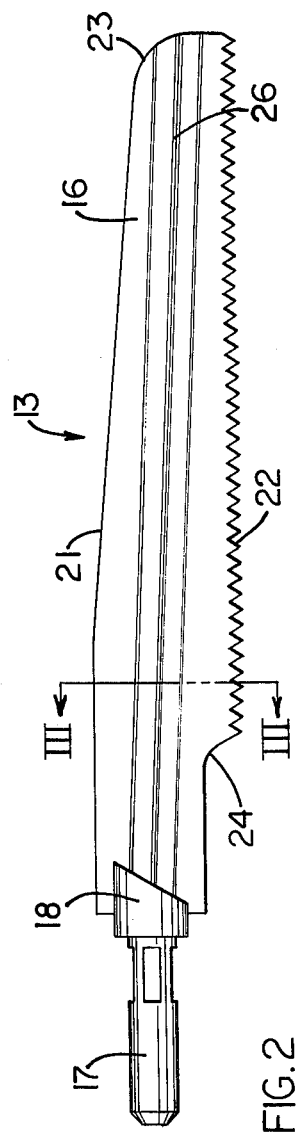
FIG.2
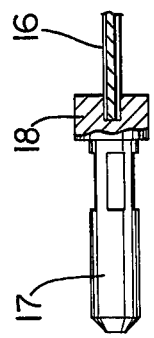
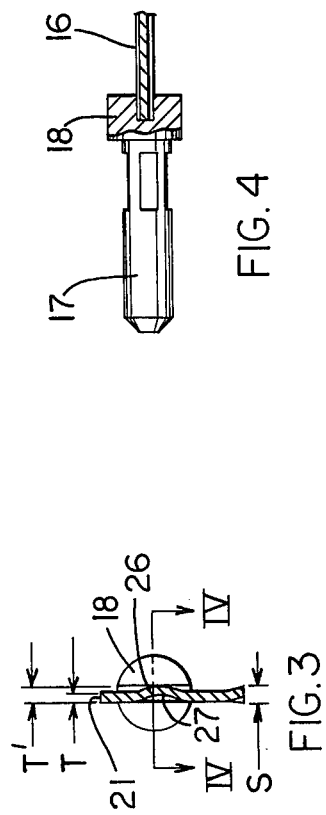
FIG.3
FIG.4

SURGICAL SAW

BACKGROUND OF THE INVENTION

Persons acquainted with surgical saws and their use are familiar with the fact that it is desirable to furnish bone saws which are as thin as reasonably possible. The reason for this is to minimize the amount of bone which is removed during the sawing operation and thereby promote swifter healing. However, it has been found that thin blades tend to whip and deflect excessively during a cutting operation, thereby impeding such cutting operation and, in some instances, forcing the use of a considerably thicker blade. However, when a thick blade is used in order to avoid the deflection problems, then the width of the teeth must be increased materially in order to prevent seizing of the blade by the bone being cut. The result, of course, is a considerably larger or wider cut than desirable. This problem is especially present with elongated saw blades of the type which are reciprocated lengthwise to effect a cutting operation.

Accordingly, a primary object of this invention is the provision of a relatively thin saw blade for a surgical saw, which blade is so constructed to avoid the whipping and deflecting action which would normally occur with a blade of such thickness.

Other objects and purposes of this invention will become apparent to persons familiar with this type of equipment upon reading the following specification and examining the accompanying drawings.

BRIEF DESCRIPTION OF THE DRAWINGS

FIG. 1 is a perspective view of a handpiece with a blade mounted thereon.

FIG. 2 is a side elevational view of the blade apart from the handpiece.

FIG. 3 is an enlarged sectional view taken along the line III—III in FIG. 2.

FIG. 4 is a fragmentary sectional view taken along the line IV—IV in FIG. 3.

SUMMARY OF THE INVENTION

The objects and purposes of the invention, including those set forth above, have been met by providing an elongated and relatively thin surgical saw blade having saw teeth along one edge thereof and an offset ridge portion extending lengthwise of the blade and spaced intermediate the edges thereof. The offset portion is only on one side of the blade. A shank is secured to one end of the blade and is engageable with a chuck and a handpiece having drive means for effecting lengthwise reciprocation of the blade.

DETAILED DESCRIPTION

FIG. 1 illustrates therein the surgical saw 10 defined by a handpiece 11 having a chuck 12 associated with one end thereof. An elongated blade structure 13 is adapted to be mounted on the handpiece by means of the chuck. The handpiece contains therein a driving mechanism (not shown) of conventional construction for effecting reciprocating movement of the blade structure 13 in the longitudinal direction thereof to permit the performance of a cutting operation, such as on the bone of a human. The handpiece 11 and the manner in which it mounts and drivingly reciprocates the blade is well known.

Considering now the improved blade structure 13, same comprises a blade 16 having an elongated shank or adapter 17 fixedly secured to one end thereof. The shank 17 is of a substantially cylindrical configuration and is adapted to project into the end of the handpiece so as to be drivingly connected to the drive means associated therewith. The shank has a cylindrical hub 18 assoiated with the forward end thereof, which hub has a slot into which projects the rearward end of the blade 16, whereupon the blade 16 is suitably fixedly secured to the hub 18, as by being soldered thereto. The blade 16 comprises an elongated platelike member having opposite longitudinally extending edges 21 and 22. The edge 22 comprises the toothed edge of the blade and is formed by a plurality of conventional teeth. The forward end of the blade has a curved edge 23 thereon which merges smoothly with the upper longitudinally extending edge 21 and then curves downwardly so as to intersect the toothed edge 22 at a rather substantial angle, such as approximately a right angle. The toothed edge 22 projects from the forward end of the blade to a location spaced from the rear end of the blade, whereupon the toothed edge terminates in a curved surface 24 which defines a relief area adjacent the rearward end of the blade.

The blade 16 is formed from a platelike member of substantially uniform thickness, whereupon the blade is thus of substantially uniform thickness as designated by the dimension T, which thickness is normally in the range of 0.012 to 0.020 of an inch, and is normally approximately 0.015 of an inch. However, as is conventional, the set of the toothed edge, that is the width across the toothed edge as indicated by the dimension S in FIG. 3, is substantially greater than the thickness T since the teeth 22 alternately diverge in opposite direction.

According to the present invention, the blade 16 is additionally provided with an offset portion 26 formed therein, which offset portion extends longitudinally of the blade throughout the complete length thereof and is disposed spaced from the opposite longitudinally extending edges 21 and 22. The offset 26 is of a shallow V-shaped configuration in that it projects sidewardly of the blade, that is, in a direction substantially perpendicular to the plane of the blade. This offset 26 projects outwardly from only one side of the blade (the rightward side in FIG. 3), thereby resulting in the formation of a shallow groove or crease 27 extending longitudinally along the other side of the blade (the leftward side in FIG. 3). The offset portion 26 is of the same thickness T as the blade but projects sidewardly of the blade through a distance which results in the blade structure having an overall thickness T' which is equal to the thickness T plus the magnitude of the offset 26. However, this overall thickness T' is no larger than the tooth set S so as to avoid binding of the blade on the bone during a cutting operation.

In the present invention, the overall thickness T' is normally in the range of between 0.032 and 0.035 of an inch, and is preferably approximately 0.0335 of an inch.

The offset portion 26, and the resulting groove or crease 27 formed therebehind, is positioned substantially midway between the upper and lower edges 21 and 22, respectively, as indicated in FIG. 2. Further, the offset portion 26 is received within the slot formed in the hub 18 so that when the hub 18 and blade are soldered together, a strong and rigid connection can be achieved therebetween.

The presence of the offset portion 26 greatly increases the strength of the blade, and particularly increases the resistance of the blade to whip and deflection. However, since the overall thickness T' of the blade is still no larger than the set or thickness S of the toothed edge, a blade of minimum thinness is still provided so as to minimize the amount of bone which is removed during the sawing operation, while at the same time not causing undesirable binding or seizing of the blade by the bone being cut.

Although a particular preferred embodiment of the invention has been disclosed in detail for illustrative purposes, it will be recognized that variations or modifications of the disclosed apparatus, including the rearrangement of the parts, lie within the scope of the present invention.

The embodiments of the invention in which an exclusive property or privilege is claimed are defined as follows:

1. In a surgical saw having a handpiece, a chuck on said handpiece and drive means for effecting reciprocating movement of said chuck axially thereof, the combination comprising:

elongated, relatively thin blade means having sidewardly offset saw teeth along one lengthwise edge thereof and an integral offset portion extending lengthwise of said blade means throughout the length thereof and disposed intermediate between and spaced from the lengthwise edges thereof, the overall thickness of said blade means, as measured across the offset portion, being no greater than the thickness as measured transversely across the offset toothed edge;

said offset portion being of a shallow V-shaped configuration and projecting outwardly of said blade means from only one side thereof, the other side of said blade means having a shallow groove formed therein as defined within said offset portion, said offset portion and the remaining portions of said blade means, except for the toothed edge, being of a substantially uniform material thickness; and shank means rigidly and fixedly secured to one end of said blade means and projecting longitudinally thereof, said shank means having an enlarged portion provided with a slot extending thereacross, and said one end of said blade means being snugly disposed within said slot and fixedly connected to said enlarged portion, said shank means being engageable by said chuck whereby said blade means can be reciprocated lengthwise thereof by said drive means.

2. A saw accoring to claim 1, wherein the edges of said blade means converge away from said shank means; and wherein the thickness of the material forming said blade means is in the range of between 0.012 and 0.020 of an inch and the overall thickness of said blade means and said offset means is in the range between 0.032 and 0.035 of an inch.

* * * * *